United States Patent
Johnson

(10) Patent No.: US 9,474,219 B2
(45) Date of Patent: Oct. 25, 2016

(54) SQUASH HYBRID SV0201YL AND PARENTS THEREOF

(71) Applicant: SEMINIS VEGETABLE SEEDS, INC., St. Louis, MO (US)

(72) Inventor: William Clyde Johnson, Sacramento, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 310 days.

(21) Appl. No.: 14/094,692

(22) Filed: Dec. 2, 2013

(65) Prior Publication Data

US 2014/0157449 A1  Jun. 5, 2014

Related U.S. Application Data

(60) Provisional application No. 61/732,204, filed on Nov. 30, 2012.

(51) Int. Cl.
*A01H 5/08* (2006.01)

(52) U.S. Cl.
CPC ........................ *A01H 5/08* (2013.01)

(58) Field of Classification Search
None
See application file for complete search history.

(56) References Cited

U.S. PATENT DOCUMENTS

| | | | | |
|---|---|---|---|---|
| 6,916,974 B2 * | 7/2005 | Superak | .................. | A01H 5/08 435/410 |
| 7,432,420 B2 * | 10/2008 | Johnson | .................. | A01H 5/08 435/419 |
| 8,288,617 B2 | 10/2012 | Johnson | | |
| 2005/0159084 A1 | 7/2005 | Basol et al. | | |
| 2012/0137380 A1 * | 5/2012 | Johnson | .................. | A01H 5/08 800/260 |
| 2014/0157447 A1 * | 6/2014 | Johnson | .................. | A01H 5/08 800/260 |
| 2014/0157449 A1 * | 6/2014 | Johnson | .................. | A01H 5/08 800/260 |
| 2015/0020230 A1 * | 1/2015 | Johnson | .................. | A01H 5/08 800/260 |

OTHER PUBLICATIONS

U.S. Appl. No. 10/761,877, Basol et al.
U.S. Appl. No. 12/197,908, Johnson.
Moose SP, Mumm RH., "Molecular plant breeding as the foundation for 21st century crop improvement", Plant Physiol.; 147(3):969-77; Jul. 2008.
Variety specific information as indicated in transmittal letter of May 7, 2014 Information Disclosure Statement for U.S. Appl. No. 14/094,692.

* cited by examiner

*Primary Examiner* — Anne Kubelik
(74) *Attorney, Agent, or Firm* — Dentons US LLP; Alissa Eagle, Esq.

(57) ABSTRACT

The invention provides seed and plants of squash hybrid SV0201YL and the parent lines thereof. The invention thus relates to the plants, seeds and tissue cultures of squash hybrid SV0201YL and the parent lines thereof, and to methods for producing a squash plant produced by crossing such plants with themselves or with another squash plant, such as a plant of another genotype. The invention further relates to seeds and plants produced by such crossing. The invention further relates to parts of such plants, including the fruit and gametes of such plants.

32 Claims, No Drawings

SQUASH HYBRID SV0201YL AND PARENTS THEREOF

CROSS-REFERENCE TO RELATED APPLICATIONS

This application claims the priority of U.S. Provisional Appl. Ser. No. 61/732,204, filed Nov. 30, 2012, the entire disclosure of which is incorporated herein by reference.

FIELD OF THE INVENTION

The present invention relates to the field of plant breeding and, more specifically, to the development of squash hybrid SV0201YL and the inbred squash lines LEB-EH-08-877 and ZGN-130-1091.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a squash plant of the hybrid designated SV0201YL, the squash line LEB-EH-08-877 or squash line ZGN-130-1091. Also provided are squash plants having all the physiological and morphological characteristics of such a plant. Parts of these squash plants are also provided, for example, including pollen, an ovule, scion, a rootstock, a fruit, and a cell of the plant.

In another aspect of the invention, a plant of squash hybrid SV0201YL and/or squash lines LEB-EH-08-877 and ZGN-130-1091 comprising an added heritable trait is provided. The heritable trait may comprise a genetic locus that is, for example, a dominant or recessive allele. In one embodiment of the invention, a plant of squash hybrid SV0201YL and/or squash lines LEB-EH-08-877 and ZGN-130-1091 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of squash hybrid SV0201YL and/or squash lines LEB-EH-08-877 and ZGN-130-1091. The squash seed of the invention may be provided as an essentially homogeneous population of squash seed of squash hybrid SV0201YL and/or squash lines LEB-EH-08-877 and ZGN-130-1091. Essentially homogeneous populations of seed are generally free from substantial numbers of other seed. Therefore, seed of hybrid SV0201YL and/or squash lines LEB-EH-08-877 and ZGN-130-1091 may be defined as forming at least about 97% of the total seed, including at least about 98%, 99% or more of the seed. The seed population may be separately grown to provide an essentially homogeneous population of squash plants designated SV0201YL and/or squash lines LEB-EH-08-877 and ZGN-130-1091.

In yet another aspect of the invention, a tissue culture of regenerable cells of a squash plant of hybrid SV0201YL and/or squash lines LEB-EH-08-877 and ZGN-130-1091 is provided. The tissue culture will preferably be capable of regenerating squash plants capable of expressing all of the physiological and morphological characteristics of the starting plant, and of regenerating plants having substantially the same genotype as the starting plant. Examples of some of the physiological and morphological characteristics of the hybrid SV0201YL and/or squash lines LEB-EH-08-877 and ZGN-130-1091 include those traits set forth in the tables herein. The regenerable cells in such tissue cultures may be derived, for example, from embryos, meristems, cotyledons, pollen, leaves, anthers, roots, root tips, pistils, flowers, seed and stalks. Still further, the present invention provides squash plants regenerated from a tissue culture of the invention, the plants having all the physiological and morphological characteristics of hybrid SV0201YL and/or squash lines LEB-EH-08-877 and ZGN-130-1091.

In still yet another aspect of the invention, processes are provided for producing squash seeds, plants and fruit, which processes generally comprise crossing a first parent squash plant with a second parent squash plant, wherein at least one of the first or second parent squash plants is a plant of squash line LEB-EH-08-877 or squash line ZGN-130-1091. These processes may be further exemplified as processes for preparing hybrid squash seed or plants, wherein a first squash plant is crossed with a second squash plant of a different, distinct genotype to provide a hybrid that has, as one of its parents, a plant of squash line LEB-EH-08-877 or squash line ZGN-130-1091. In these processes, crossing will result in the production of seed. The seed production occurs regardless of whether the seed is collected or not.

In one embodiment of the invention, the first step in "crossing" comprises planting seeds of a first and second parent squash plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent squash plants into plants that bear flowers. A third step may comprise preventing self-pollination of the plants, such as by emasculating the flowers (i.e., killing or removing the pollen).

A fourth step for a hybrid cross may comprise cross-pollination between the first and second parent squash plants. Yet another step comprises harvesting the seeds from at least one of the parent squash plants. The harvested seed can be grown to produce a squash plant or hybrid squash plant.

The present invention also provides the squash seeds and plants produced by a process that comprises crossing a first parent squash plant with a second parent squash plant, wherein at least one of the first or second parent squash plants is a plant of squash hybrid SV0201YL and/or squash lines LEB-EH-08-877 and ZGN-130-1091. In one embodiment of the invention, squash seed and plants produced by the process are first generation ($F_1$) hybrid squash seed and plants produced by crossing a plant in accordance with the invention with another, distinct plant. The present invention further contemplates plant parts of such an $F_1$ hybrid squash plant, and methods of use thereof. Therefore, certain exemplary embodiments of the invention provide an $F_1$ hybrid squash plant and seed thereof.

In still yet another aspect, the present invention provides a method of producing a plant derived from hybrid SV0201YL and/or squash lines LEB-EH-08-877 and ZGN-130-1091, the method comprising the steps of: (a) preparing a progeny plant derived from hybrid SV0201YL and/or squash lines LEB-EH-08-877 and ZGN-130-1091, wherein said preparing comprises crossing a plant of the hybrid SV0201YL and/or squash lines LEB-EH-08-877 and ZGN-130-1091 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid SV0201YL and/or squash lines LEB-EH-08-877 and ZGN-130-1091. The plant derived from hybrid SV0201YL and/or squash lines LEB-EH-08-877 and ZGN-130-1091 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid SV0201YL and/or squash lines LEB-EH-08-877 and ZGN-130-1091 is obtained which possesses some of the desirable traits of the line/hybrid as well as potentially other selected traits.

In certain embodiments, the present invention provides a method of producing food or feed comprising: (a) obtaining a plant of squash hybrid SV0201YL and/or squash lines LEB-EH-08-877 and ZGN-130-1091, wherein the plant has been cultivated to maturity, and (b) collecting at least one squash from the plant.

In still yet another aspect of the invention, the genetic complement of squash hybrid SV0201YL and/or squash lines LEB-EH-08-877 and ZGN-130-1091 is provided. The phrase "genetic complement" is used to refer to the aggregate of nucleotide sequences, the expression of which sequences defines the phenotype of, in the present case, a squash plant, or a cell or tissue of that plant. A genetic complement thus represents the genetic makeup of a cell, tissue or plant, and a hybrid genetic complement represents the genetic make up of a hybrid cell, tissue or plant. The invention thus provides squash plant cells that have a genetic complement in accordance with the squash plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid SV0201YL and/or squash lines LEB-EH-08-877 and ZGN-130-1091 could be identified by any of the many well known techniques such as, for example, Simple Sequence Length Polymorphisms (SSLPs) (Williams et al., *Nucleic Acids Res.,* 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In still yet another aspect, the present invention provides hybrid genetic complements, as represented by squash plant cells, tissues, plants, and seeds, formed by the combination of a haploid genetic complement of a squash plant of the invention with a haploid genetic complement of a second squash plant, preferably, another, distinct squash plant. In another aspect, the present invention provides a squash plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of squash hybrid SV0201YL, squash line LEB-EH-08-877 and squash line ZGN-130-1091.

Squash hybrid SV0201YL, also known as LEBEHH0201, is a long Lebanese-type squash, similar to the market class known best by the commercial products Eskenderany, Otto, Revera, and Marzouka. SV0201YL has uniform cylindrical fruit, somewhat darker in color than some other hybrids, a very vigorous growth habit, and resistance for at least 3 important viral diseases: ZYMV, WMV, and SLCV.

A. Origin and Breeding History of Squash Hybrid SV0201YL

The parents of hybrid SV0201YL are LEB-EH-08-877 and ZGN-130-1091. These parents were created as follows:

Squash line LEB-EH-08-877 was developed by 10 generations of inbreeding following a cross of the proprietary inbred line LEB-47-5004 and LEB-47-103.

Selection of inbred line LEB-EH-08-877 required the following germplasm sources: (1 and 2) distinct selections from Turkish landraces of squash known locally as "beyaz kabak", (3) a selection from the common landrace "Small Green Algerian," and (4) the diverse F1 family known as "ZUCX85-187-3" distributed by Henry Munger of Cornell University in 1986.

LEB-EH-08-877 traces lineage back to ZUCX85-187-3. In 1986 an individual plant selection from the diverse F1 family known as ZUCX85-187-3 was crossed to the landrace "Small Green Algerian." An individual plant from this family was selected and used as a male parent in a cross with a selection from the "Small Green Algerian" landrace. The F1 seed from this cross was self pollinated, and between 1987 and 1992 was advanced to the F8 generation at breeding nurseries in New Jersey and Florida, guided by progeny testing results with ZYMV and WMV screening. In 1994 an F7 selection from this lineage was artificially inoculated at Woodland Calif. with ZYMV, and the family was observed to be uniformly resistant. A surviving plant from that screen was used as the female parent in a cross to a selection of the landrace "beyaz kabak", and the resulting F1 hybrid was self pollinated at a greenhouse in Woodland, Calif. In 1995 the F2 generation was inoculated with ZYMV, and survivors were selected for conformity to the Lebanese ideotype (white fruit color, thick leaves, strong canopy, high vigor). The same screen was repeated on the F3 generation in 1996. The F4 and F5 generations were selected and self pollinated based only on phenotypic conformity to the Lebanese ideotype. In 1997 four individual plants from the F6 generation showing phenotypic uniformity were selected and bulked to create the proprietary inbred line LEB-47-5004.

In 1998 the proprietary inbred LEB-47-5004 was shared with the squash breeding program of the legacy company of Royal Sluis in Nimes, France. LEB-47-5004 was then hybridized to a different selection of the landrace known as "beyaz kabak," and between 1998 and 2006 ten generations of selection and self pollination with progeny testing for resistance to ZYMV and WMV were performed to recombine the resistance to potyviruses found LEB-47-5004 with a fruit shape and color that better adheres to the Lebanese ideotype. In 2008 the self pollinated progeny of a single F11 generation plant was designated as LEB-EH-08-877, and all subsequent testing and hybrids were developed from the progeny of that source.

Squash line ZGN-130-1091 was developed by a selection strategy involving five primary components: (1) ZGN-130-1003, a proprietary breeding line contributing fruit quality characteristics and some potyvirus resistance that is itself derived directly from the commercial hybrid "Tigress", (2) ZGY-46-2604, the original gray zucchini source of resistance to SLCV, which was distributed by Sergio Garza from the Universidad de Sonora in Hermosillo, Sonora, Mexico, in 1998, (3) G710, a proprietary breeding line contributing fruit quality characteristics, derived from the commercial hybrid "Black Beauty", (4) HP13HMW/HP134*1, a breeding line contributing high resistance to ZYMV, WMV-2, and PRSV, and (5) the proprietary inbred ZGN-130-1020, a vigorous green zucchini parent line with resistance to ZYMV and WMV-2. ZGN-130-1091 is derived from germplasm with high levels of resistance to SLCV, an unexpected result of the combination of low levels of resistance from ZGY 46-2604 and the SLCV susceptible breeding line HP13HMW/HP134*1. ZGN-130-1091 is derived from germplasm with high levels of resistance to SLCV, an unexpected result of the combination of low levels of resistance from ZGY 46-2604 and the SLCV susceptible breeding line HP13HMW/HP134*1, which is the subject of different intellectual property filings, U.S. application Ser. No. 10/761,877 and U.S. Pat. No. 8,288,617 (from U.S. patent application Ser. No. 12/197,908).

ZGY-46-2604 was crossed to a series of breeding lines, including G710 in order to develop breeding populations with a combination of SLCV resistance and acceptable fruit types. The resulting F1 progeny of this cross was backcrossed to G710, and the BC1F2, BC1F3, and BC1F4 generations were selected for fruit and plant characteristics without regard to SLCV virus resistance in Tifton, Ga.

The self-pollinated BC1F5 progeny selections were included in a field trial in the Rio Grande Valley of Texas in late summer 2000 (a location and date chosen for its history of SLCV epidemics). Heavy SLCV pressure and high levels of potyvirus infestations in the same field allowed for the selections of breeding lines with SLCV and potyvirus resistance. Nineteen selections (or remnant seed in the case of failed pollinations) were chosen to be planted in the greenhouse at Woodland, Calif. in February, 2001 and inoculated with SLCV. Four BC1F5 and BC1F6 families were selected for a high level of resistance to SLCV and for fruit quality characteristics.

The selected families were crossed to a series of thirty-one breeding lines in the spring of 2001. During the summer of 2001, these breeding lines were evaluated for virus resistance through individual and cocktail screens of potyviruses and for fruit quality characteristics in Woodland, Calif. Ten hybrids were selected, and these ten hybrids were subsequently evaluated for resistance to SLCV in a nursery planted in Hermosillo, Mexico in the latter part of 2001. The hybrid (ZGN-130-1003/(ZGY-46-2604/G710*1)) was selected for development of new germplasm. This hybrid was planted in the greenhouse at Woodland, Calif. in February of 2002, and was crossed to proprietary inbred line HP13HMW/HP134*1.

The resulting F1 population, known as (ZGN-130-1003/(ZGY-46-2604/G710*1F6))/(HP13HMW/HP134*1), was inoculated with a cocktail of ZYMV, WMV-2, and PRSV, and survivors were moved to the field in Woodland, Calif. in the summer of 2002. This survivor population and all its progeny were named TAW. Thirty-seven individuals were selected from the TAW population based on potyvirus resistance and fruit and plant characteristics. The F2 generations from these thirty seven selections were sown in the greenhouse in Woodland, Calif. in January 2003, and inoculated with ZYMV, WMV-2, PRSV, and SLCV.

The high SLCV resistance described was first observed in this early 2003 screen, where F2 individuals in certain families showed much higher levels of resistance to SLCV than the original source of resistance, ZGY-46-2604. These F2 individuals were self-pollinated.

F3 families derived from the F2 individuals with unexpectedly high levels of SLCV resistance were inoculated with a cocktail of ZYMV, WMV-2, and PRSV, and resistant individuals were transplanted to a field near Woodland, Calif. in the summer of 2003. One hundred and two F3 individuals were selected for self-pollination from this field based on their level of potyvirus resistance, and fruit and plant characteristics. Successful pollinations from the California F3 generation were sown in Florida to evaluate fruit quality and Sinaloa (for a simultaneous observation under heavy potyvirus and geminivirus natural pressure), and ten F4 families were selected. The field trial in Sinaloa allowed verification of the high level geminivirus resistance in an environment very similar to a commercial field. The selected lines provided a verification of the unexpected results from the early 2003 greenhouse screen, because the F4 generation also showed a higher level of resistance to natural geminivirus infection than the genotype which was the original source of resistance.

Simultaneously with the F3 family testing with ZYMV, WMV-2, and PRSV, these same F3 families were also sent for crosses with elite proprietary inbred lines, including the cross that eventually led to ZGN-130-1091. When results of the testing from F3 and F4 generation experiments in Woodland and Sinaloa were completed, the TAW F3 families with the best levels of resistance for potyvirus and geminivirus had already been crossed to a battery of elite inbred lines. One of those elite inbred lines was ZGN-130-1020. ZGN-130-1020 was developed from a cross between the Italian landrace known as "Verde Milano Migliorato" and "HMZYR" that was distributed by Cornell University through 8 generations of selection, self pollination, and backcrossing (to "Verde Milano Migliorato"). The hybrid developed by one elite cross from a TAW F3 selection and ZGN-130-1020 was self pollinated in the greenhouse in Woodland Calif. in 2004, and the F2 generation was evaluated in late 2004 at Felda, Fla. Individual plants were selected and self-pollinated based on phenotype, with the individuals most like a green zucchini ideotype selected (highly productive, short internode length, erect growth habit, early maturity, cylindrical immature fruit shape). The F3 generation was inoculated with ZYMV, WMV, and SLCV in early 2005, and survivors were individually self pollinated in a greenhouse generation.

In the F4 generation no intentional selection pressure was applied during a greenhouse generation increase. The F5 generation was inoculated with a cocktail of ZYMV, WMV, and PRSV, and survivors were grown in Woodland, Calif. Individual plant selections were based on resistance to viral infection and adherence to the green zucchini ideotype. The F6 generation was planted in the greenhouse at Woodland, Calif. in early 2006, and artificially inoculated with SLCV. The progeny showed uniform resistance to SLCV, and individual plants were self pollinated to create the F7. The F7 generation was increased and individually self pollinated without additional screening in late 2006. In the F8 generation seedlings were artificially inoculated with a cocktail of ZYMV, WMV, and PRSV, and were observed to be uniformly resistant. An individual plant from this F8 generation screen was self pollinated, and designated as ZGN-130-1091. ZGN-130-1091 derives from the progeny of a single F8 generation self-pollinated plant.

The parent lines are uniform and stable, as is a hybrid produced therefrom. A small percentage of variants can occur within commercially acceptable limits for almost any characteristic during the course of repeated multiplication. However no variants are expected.

B. Physiological and Morphological Characteristics of Squash Hybrid SV0201YL, Squash Line LEB-EH-08-877 and Squash Line ZGN-130-1091

In accordance with one aspect of the present invention, there is provided a plant having the physiological and morphological characteristics of squash hybrid SV0201YL and the parent lines thereof. A description of the physiological and morphological characteristics of such plants is presented in Tables 1-3.

TABLE 1

Physiological and Morphological Characteristics of Hybrid SV0201YL

| CHARACTERISTIC | SV0201YL | Comparison Variety Anita |
|---|---|---|
| 1. Species | Pepo | Pepo |
| 2. Kind/Use | squash | squash |
| 3. Type | summer (vegetable marrow) | summer |
| 4. Cotyledon | | |
| length | 39.9 mm | 36.9 mm |
| width | 27.8 mm | 25.5 mm |
| apex | rounded | tapered |
| veining | plainly visible | plainly visible |
| color | medium green | medium green |
| color (RHS Color Chart) | 143A | 143B |
| Seedling | | |
| shape of cotyledons | elliptic (Cora, Tivoli) | elliptic |
| intensity of green color of cotyledons | medium (Cora) | medium |
| cross section of cotyledons | concave | concave |

TABLE 1-continued

Physiological and Morphological Characteristics of Hybrid SV0201YL

| CHARACTERISTIC | SV0201YL | Comparison Variety Anita |
|---|---|---|
| 5. Mature Plant | | |
| growth habit | bush | bush |
| plant type | prickly | prickly |
| 6. Main Stem | | |
| cross-section shape | angled | angled |
| diameter at mid-point of $1^{st}$ internode | 24.5 mm | 26.1 mm |
| average length | 43.0 cm | 66 cm |
| average number of internodes | 17.5 | 20.7 |
| Stem | | |
| color | completely green (Becky) | completely green |
| intensity of green color | dark (Greyzini) | dark |
| mottling | absent (Cinderella) | present |
| tendrils | well developed (Baby Bear, Greyzini) | well developed |
| Plant | | |
| growth habit | bush (Greyzini) | bush |
| branching | absent (Goldi) | absent |
| bush varieties only: attitude of petiole (excluding lower external leaves) | semi-erect (Arlesa) | semi-erect to horizontal |
| 7. Leaves | | |
| blade shape | reniform | reniform |
| blade form | deep lobed | deep lobed |
| margin | denticulate | denticulate |
| margin edges | frilled | frilled |
| average width | 35.2 cm | 38.4 cm |
| average length | 28.8 cm | 29.6 cm |
| leaf surface | blistered | blistered |
| dorsal surface pubescence | soft hairy | bristled |
| vental surface pubescence | soft hairy | bristled |
| color | dark green | dark green |
| color (RHS Color Chart) | 147A | 147A |
| leaf blotching | blotched with gray | blotched with gray |
| leaf blade: size | medium (Ambassador) | medium |
| leaf blade: incisions | medium (Jackpot) | medium |
| leaf blade: intensity of green color of upper surface | dark (Everest) | dark |
| leaf blade: silvery patches | present (Civac) | present |
| leaf blade: relative area covered by silvery patches | medium (Ambassador) | large |
| average petiole length | 34.6 cm | 39.7 cm |
| petiole length | medium (Goldi) | medium |
| petiole: number of prickles | many (White Bush Scallop) | many |
| 8. Flower | | |
| pistillate flower: average diameter | 15.2 cm | 13.2 cm |
| pistillate flower: ovary | drum-like | drum-like |
| pistillate flower: average pedicel length | 1.2 cm | 6.5 cm |
| pistillate flower: margin shape | curved | curved |
| pistillate flower: margin edges | frilled | frilled |
| pistillate flower: average sepal width | 1.3 mm | 1.3 mm |
| pistillate flower: average sepal length | 4.6 mm | 6.5 mm |
| pistillate flower: color | deep yellow orange | orange |
| pistillate flower: color (RHS Color Chart) | 21A | 23A |
| staminate flower: average sepal length | 17.6 mm | 17.1 mm |
| staminate flower: average sepal width | 2.4 mm | 2.7 mm |
| staminate flower: average pedicel length | 165 mm | 169.6 mm |

TABLE 1-continued

Physiological and Morphological Characteristics of Hybrid SV0201YL

| | CHARACTERISTIC | SV0201YL | Comparison Variety Anita |
|---|---|---|---|
| | staminate flower: color | orange | orange |
| | female flower: ring at inner side of corolla | present (Aurore) | present |
| | female flower: color of ring at inner side of corolla | green (Aurore, Early White Bush Scallop, President) | green |
| | female flower: intensity of green color of ring at inner side of corolla (varieties with green ring at inner side of corolla) | strong (Aristocrat, Diamant) | weak |
| | male flower: ring at inner side of corolla | present (Goldi) | present |
| | male flower: color of ring at inner side of corolla | green (Austral, Belor, Goldi) | yellow and green |
| | male flower: intensity of green color of ring at inner side of corolla | strong (Goldi) | |
| | staminate flower: color | 23A | orange |
| 9. | Fruit | | |
| | market maturity: average length | 16.3 cm | 16.1 cm |
| | market maturity: average width - stem end | 2.8 cm | 3.2 cm |
| | at market maturity: average width - blossom end | 1.3 cm | 2.2 cm |
| | market maturity: average weight | 197.4 gm | 354.6 gm |
| | market maturity: shape according to variety type | banana | butternut |
| | market maturity: apex | rounded | rounded |
| | market maturity: base | rounded | rounded |
| | market maturity: ribs | none | inconspicuous |
| | market maturity: rib furrow depth | shallow | shallow |
| | market maturity: rib furrow width | narrow | narrow |
| | market maturity: fruit surface | smooth | fine wrinkle |
| | market maturity: warts | none | none |
| | market maturity: blossom scar button | raised acorn | raised acorn |
| | young fruit: ratio length/maximum diameter (zucchini type varieties) | large (Carlotta) | medium |
| | young fruit: general shape (zucchini and rounded zucchini type varieties) | tapered elliptical (Top Kapi) | tapered elliptical |
| | young fruit: main color of skin (excluding color of ribs or grooves) | green (Elite, Opal, Romano) | green |
| | young fruit: intensity of green color of skin (only varieties with green color of skin) | medium (Baccara) | light |
| | general shape | club shaped | club shaped |
| | length (zucchini type varieties) | medium (Cora) | medium |
| | maximum diameter (zucchini type varieties) | small (Goldi) | medium |
| | ratio length/maximum diameter (zucchini type varieties) | small (Jedida) | medium |
| | blossom end (zucchini and neck type varieties) | rounded | rounded |
| | grooves | present | absent |
| | depth of grooves | shallow (Connecticut Field) | |
| | ribs | absent | absent |
| | main color of skin (excluding color of dots, patches, stripes and bands) | green (Ambassador, Baby Bear) | green |
| | intensity of green color of skin (only varieties with green color of skin) | medium | light |

TABLE 1-continued

Physiological and Morphological Characteristics of Hybrid SV0201YL

| CHARACTERISTIC | SV0201YL | Comparison Variety Anita |
|---|---|---|
| stripes in grooves | absent (Baby Bear, Jack Be Little) | absent |
| dots | present (Gold Rush, Table Queen) | present |
| size of main dots | medium (Grey Zucchini) | very large |
| secondary green color between ribs (excluding dots) | absent (Grey Zucchini, Small Sugar) | absent |
| warts on skin | absent | absent |
| size of flower scar | small (Goldi) | medium |
| length of peduncle | very short (Arlesa) | medium |
| color of peduncle | green (Ambassador) | green |
| intensity of green color of peduncle | dark (Gold Rush) | medium |
| mottling of peduncle | present (Elite) | present |
| ripe fruit: secondary color of skin (excluding color of mottles, patches, stripes and bands) | yellow (Gold Rush) | yellow |
| ripe fruit: intensity of main color of skin (only yellow and orange) | medium | medium |
| ripe fruit: color of flesh | yellow (Sunburst, Vegetable Spaghetti) | yellow |
| ripe fruit: lignified rind | present (Elite, Little Gem, Scallopini, Yellow Summer Crookneck) | present |
| ripe fruit: structure of flesh | fibrous (Vegetable Spaghetti) | fibrous |
| 10. Rind | | |
| average thickness at medial | 1.9 mm | 2.2 mm |
| toughness | hard | hard |
| overall color pattern | regular | regular |
| main or ground color | orange-gray | yellowish-orange |
| main or ground color (RHS Color Chart) | 163D | 18D |
| color of stripes | creamy-yellow | creamy-orange |
| RHS Color Chart for spots color | 19B | 20C |
| pattern of spots | not specific | not specific |
| 11. Flesh | | |
| average blossom end thickness | 35.9 mm | 60.3 mm |
| average medial thickness | 40.5 mm | 55.6 mm |
| average stem end thickness | 39.3 mm | 44.4 mm |
| texture (fine, granular, lumpy or stringy) | fine | fine |
| texture (soft, firm or brittle) | soft | firm |
| texture (dry, moist or juicy) | juicy | juicy |
| flavor | sweet | sweet |
| quality | excellent | good |
| color | creamy-white | creamy-white |
| color (RHS Color Chart) | 155A | 155B |
| 12. Seed Cavity | | |
| average length | 30.7 cm | 24.6 cm |
| average width | 6.5 cm | 7.9 cm |
| location | conforms to fruit shape | conforms to fruit shape |
| placental tissue | abundant | moderately abundant |
| center core | prominent | prominent |
| 13. Fruit Stalks | | |
| average length | 1.4 cm | 3.2 cm |
| average diameter | 2.4 cm | 2.4 cm |
| cross-section shape | irregular | irregular |
| twisting | not twisted | not twisted |
| tapering | tapered | tapered |
| straightness | slightly curved | slightly curved |
| texture | hard | hard |
| furrows | shallow | deep |
| surface | smooth | spiny |
| attachment end | slightly expanded | expanded |
| detaches | with difficulty | with difficulty |

TABLE 1-continued

Physiological and Morphological Characteristics of Hybrid SV0201YL

| CHARACTERISTIC | SV0201YL | Comparison Variety Anita |
|---|---|---|
| color | medium green | medium green |
| color (RHS Color Chart) | 141C | 143A |
| 14. Seeds | | |
| average length | 15.8 mm | 16.8 mm |
| average width | 9.4 mm | 9.8 mm |
| average thickness | 2.8 mm | 3.3 mm |
| face surface | smooth | smooth |
| color | cream | cream |
| color (RHS Color Chart) | 160D | 155A |
| luster | dull | glossy |
| margin | curved | curved |
| margin edge | rounded | rounded |
| separation from pulp | difficult | easy |
| average grams per 100 seeds | 16.0 gm | 18.0 gm |
| average number of seeds per fruit | 199.8 | 138.6 |
| seed coat | normal | normal |
| size | medium (Diamant) | large |
| shape | broad elliptic (Baby Boo) | elliptic |
| hull | present (Baby Bear, Elite) | present |
| appearance of hull | fully developed (Elite) | fully developed |
| color of hull | cream (De Nice à Fruit Rond) | cream |
| fruit type: | zucchini | |
| fruit: patches, stripes or bands in ripe stage (if zucchini type) | absent (Ambassador, Black Jack) | |

*These are typical values. Values may vary due to environment. Other values that are substantially equivalent are also within the scope of the invention.

TABLE 2

Physiological and Morphological Characteristics of Line ZGN-130-1091

| CHARACTERISTIC | ZGN 130-1091 | Comparison Variety Payroll |
|---|---|---|
| 1. Species | Pepo | Pepo |
| 2. Kind/Use | squash | squash |
| 3. Type | summer (vegetable marrow) | summer |
| 4. Cotyledon | | |
| length | 39.4 mm | 44.27 mm |
| width | 29.4 mm | 29.13 mm |
| apex | rounded | rounded |
| veining | plainly visible | plainly visible |
| color | medium green | dark green |
| color (RHS Color Chart) | 137A | 147A |
| Seedling | | |
| shape of cotyledons | elliptic (Cora, Tivoli) | elliptic |
| intensity of green color of cotyledons | medium (Cora) | dark |
| cross section of cotyledons | straight (Sunburst) | straight |
| 5. Mature Plant | | |
| growth habit | bush | bush |
| plant type | prickly | prickly |
| 6. Main Stem | | |
| cross-section shape | angled | round |
| diameter at mid-point of 1st internode | 33 mm | 29.79 mm |
| average length | 35 cm | 38.6 cm |
| average number of internodes | 36 | 28.56 |
| Stem | | |
| color | completely green (Becky) | completely green |
| intensity of green color | very dark (Goldrush) | dark |
| mottling | absent (Cinderella) | present |
| tendrils | absent to rudimentary (Goldrush, Sylvana) | absent to rudimentary |

TABLE 2-continued

Physiological and Morphological Characteristics of Line ZGN-130-1091

| CHARACTERISTIC | ZGN 130-1091 | Comparison Variety Payroll |
|---|---|---|
| Plant | | |
| growth habit | bush (Greyzini) | bush |
| branching | present (Patty Green Tint) | absent |
| degree of branching | weak (Karioka, Verdi) | |
| bush varieties only: attitude of petiole (excluding lower external leaves) | semi-erect to horizontal (Goldi) | semi-erect to horizontal |
| 7. Leaves | | |
| blade shape | reniform | ovate |
| blade form | shallow lobed | deep lobed |
| margin | denticulate | dentate |
| margin edges | frilled | frilled |
| average width | 35 cm | 32.92 cm |
| average length | 29 cm | 28.1 cm |
| leaf surface | blistered | smooth |
| dorsal surface pubescence | soft hairy | bristled |
| vental surface pubescence | soft hairy | bristled |
| color | dark green | medium green |
| color (RHS Color Chart) | 137A | 137A |
| leaf blotching | blotched with gray | blotched with gray |
| leaf blade: size | medium (Ambassador) | large |
| leaf blade: incisions | medium (Jackpot) | medium |
| leaf blade: intensity of green color of upper surface | dark (Everest) | medium |
| leaf blade: silvery patches | present (Civac) | present |
| leaf blade: relative area covered by silvery patches | medium (Ambassador) | medium |
| average petiole length | 32 cm | 33.15 cm |
| petiole length | medium (Goldi) | long |
| petiole: number of prickles | few (Opaline) | many |
| 8. Flower | | |
| pistillate flower: average diameter | 11.9 cm | 16.39 cm |
| pistillate flower: ovary | drum-like | drum-like |
| pistillate flower: average pedicel length | 1.1 cm | 2.14 cm |
| pistillate flower: margin shape | curved | curved |
| pistillate flower: margin edges | frilled | frilled |
| pistillate flower: average sepal width | 0.9 mm | 1.47 mm |
| pistillate flower: average sepal length | 3.3 mm | 6.14 mm |
| pistillate flower: color | orange | deep yellow |
| pistillate flower: color (RHS Color Chart) | 17B | 17A |
| staminate flower: average sepal length | 10.7 mm | 19.51 mm |
| staminate flower: average sepal width | 1.8 mm | 2.75 mm |
| staminate flower: average pedicel length | 117 mm | 162.53 mm |
| staminate flower: color | orange | orange |
| female flower: ring at inner side of corolla | present (Aurore) | present |
| female flower: color of ring at inner side of corolla | green (Aurore, Early White Bush Scallop, President) | yellow and green |
| female flower: intensity of green color of ring at inner side of corolla (varieties with green ring at inner side of corolla) | strong (Aristocrat, Diamant) | medium |
| male flower: ring at inner side of corolla | present (Goldi) | present |
| male flower: color of ring at inner side of corolla | green (Austral, Belor, Goldi) | yellow and green |

TABLE 2-continued

Physiological and Morphological Characteristics of Line ZGN-130-1091

| CHARACTERISTIC | ZGN 130-1091 | Comparison Variety Payroll |
|---|---|---|
| male flower: intensity of green color of ring at inner side of corolla | strong (Goldi) | medium |
| staminate flower: color | 21A | N25D |
| 9. Fruit | | |
| market maturity: average length | 19.2 cm | 15.7 cm |
| market maturity: average width - stem end | 2.5 cm | 2.53 cm |
| at market maturity: average width - blossom end | 1.1 cm | 1.56 cm |
| market maturity: average weight | 221 gm | 133.2 gm |
| market maturity: shape according to variety type | straightneck | straightneck |
| market maturity: apex | taper pointed | rounded |
| market maturity: base | rounded | rounded |
| market maturity: ribs | inconspicuous | inconspicuous |
| market maturity: rib furrow depth | shallow | shallow |
| market maturity: rib furrow width | medium wide | narrow |
| market maturity: fruit surface | smooth | smooth |
| market maturity: warts | none | none |
| market maturity: blossom scar button | raised acron | slightly extended |
| young fruit: ratio length/maximum diameter (zucchini type varieties) | large (Carlotta) | large |
| young fruit: general shape (zucchini and rounded zucchini type varieties) | cylindrical (Ambassador, Ibis) | cylindrical |
| young fruit: main color of skin (excluding color of ribs or grooves) | green (Elite, Opal, Romano) | green |
| young fruit: intensity of green color of skin (excluding color of ribs or grooves; only varieties with green color of skin) | very dark (Carnaval, Corsair) | medium |
| general shape | cylindrical | cylindrical |
| length (zucchini type varieties) | long (Carlotta) | medium |
| maximum diameter (zucchini type varieties) | small (Goldi) | medium |
| ratio length/maximum diameter (zucchini type varieties) | large (Carlotta) | large |
| blossom end (zucchini and neck type varieties) | pointed | rounded |
| grooves | absent | present |
| ribs | present | present |
| protrusion of ribs | very weak (Leda, Tivoli) | weak |
| main color of skin (excluding color of dots, patches, stripes and bands) | green (Ambassador, Baby Bear) | green |
| intensity of green color of skin (only varieties with green color of skin) | very dark (Baby Bear, Sardane) | medium |
| color of ribs compared to main color of skin | same (Grey Zucchini) | |
| dots | absent (Sunburst) | absent |
| secondary green color between ribs (excluding dots) | absent (Grey Zucchini, Small Sugar) | absent |
| warts on skin | absent | absent |
| size of flower scar | medium (Spidi) | very small |
| length of peduncle | short (Clarita) | long |
| color of peduncle | green (Ambassador) | green |
| intensity of green color of peduncle | medium (Sunburst) | medium |
| mottling of peduncle | present (Elite) | absent |
| ripe fruit: main color of | yellow (Gold Rush) | green |

TABLE 2-continued

Physiological and Morphological Characteristics of Line ZGN-130-1091

| CHARACTERISTIC | ZGN 130-1091 | Comparison Variety Payroll |
|---|---|---|
| skin (excluding color of mottles, patches, stripes and bands) | | |
| ripe fruit: intensity of main color of skin | medium | |
| ripe fruit: secondary color of skin (excluding color of mottles, patches, stripes and bands) | green | |
| ripe fruit: color of flesh | cream (Elite) | yellow |
| ripe fruit: lignified rind | present (Elite, Little Gem, Scallopini, Yellow Summer Crookneck) | present |
| ripe fruit: structure of flesh | fibrous (Vegetable Spaghetti) | fibrous |
| 10. Rind | | |
| average thickness at medial | 1.2 mm | 2.03 mm |
| toughness | hard | hard |
| overall color pattern | regular | regular |
| main or ground color | Green | greenish gray |
| main or ground color (RHS Color Chart) | N189A | N189A |
| color of blotches | orange | |
| color of blotches (RHS Color Chart) | 23A | |
| pattern of blotches | not specific | |
| 11. Flesh | | |
| average blossom end thickness | 36.7 mm | 32.4 mm |
| average medial thickness | 40.1 mm | 38.1 mm |
| average stem end thickness | 41.5 mm | 40.1 mm |
| texture (fine, granular, lumpy or stringy) | fine | stringy |
| texture (soft, firm or brittle) | firm | firm |
| texture (dry, moist or juicy) | juicy | juicy |
| flavor | insipid | insipid |
| quality | good | good |
| color | whitish cream | white |
| color (RHS Color Chart) | 8D | 155A |
| 12. Seed Cavity | | |
| average length | 34.2 cm | 34.37 cm |
| average width | 6.3 cm | 4.92 cm |
| location | conforms to fruit shape | conforms to fruit shape |
| placental tissue | abundant | abundant |
| center core | inconspicuous | prominent |
| 13. Fruit Stalks | | |
| average length | 2 cm | 2.68 cm |
| average diameter | 1.8 cm | 1.85 cm |
| cross-section shape | irregular | irregular |
| twisting | not twisted | not twisted |
| tapering | tapered | not tapered |
| straightness | slightly curved | straight |
| texture | hard | spongy |
| furrows | deep | deep |
| surface | smooth | rough |
| attachment end | expanded | slightly expanded |
| detaches | easily | easily |
| color | medium green | medium green |
| color (RHS Color Chart) | 143C | 144A |
| 14. Seeds | | |
| average length | 14.3 mm | 14.1 mm |
| average width | 8.4 mm | 8.32 mm |
| average thickness | 2.4 mm | 2.42 mm |
| face surface | smooth | smooth |
| color | white | cream |
| color (RHS Color Chart) | 155A | 162D |
| luster | glossy | dull |
| margin | curved | curved |
| margin edge | rounded | rounded |
| separation from pulp | moderately easy | easy |
| average grams per 100 | 11 gm | 11.25 gm |

TABLE 2-continued

Physiological and Morphological Characteristics of Line ZGN-130-1091

| CHARACTERISTIC | ZGN 130-1091 | Comparison Variety Payroll |
|---|---|---|
| seeds | | |
| average number of seeds per fruit | 193 | 180.25 |
| seed coat | normal | normal |
| size | small (Delicata) | medium |
| shape | broad elliptic (Baby Boo) | elliptic |
| hull | present (Baby Bear, Elite) | present |
| appearance of hull | fully developed (Elite) | rudimentary |
| color of hull | whitish (Table Queen) | cream |
| For NL Technical Questionnaire: Special Conditions for the Examination of the Variety | | |
| fruit type: | zucchini | |
| fruit: patches, stripes or bands in ripe stage (if zucchini type) | present (Elite, Greyzini) | |

*These are typical values. Values may vary due to environment. Other values that are substantially equivalent are also within the scope of the invention.

TABLE 3

Physiological and Morphological Characteristics of Line LEB-EH-08-877

| CHARACTERISTIC | LEB-EH-08-877 | Comparison Variety Anita |
|---|---|---|
| 1. Species | Pepo | Pepo |
| 2. Kind/Use | squash | squash |
| 3. Type | summer (vegetable marrow) | summer |
| 4. Cotyledon | | |
| length | 34.6 mm | 36.9 mm |
| width | 24.0 mm | 25.5 mm |
| apex | tapered | tapered |
| veining | plainly visible | plainly visible |
| color | medium green | medium green |
| color (RHS Color Chart) | 143A | 143B |
| Seedling | | |
| shape of cotyledons | narrow elliptic (Bianchini) | elliptic |
| intensity of green color of cotyledons | medium (Cora) | medium |
| cross section of cotyledons | straight (Sunburst) | concave |
| 5. Mature Plant | | |
| growth habit | bush | bush |
| plant type | prickly | prickly |
| 6. Main Stem | | |
| cross-section shape | round | angled |
| diameter at mid-point of $1^{st}$ internode | 26.7 mm | 26.1 mm |
| average length | 55.1 cm | 66 cm |
| average number of internodes | 16.4 | 20.7 |
| Stem | | |
| color | completely green (Becky) | completely green |
| intensity of green color | light (Bianchini) | dark |
| mottling | absent (Cinderella) | present |
| tendrils | absent to rudimentary (Goldrush, Sylvania) | well developed |
| Plant | | |
| growth habit | bush (Greyzini) | bush |
| branching | absent (Goldi) | absent |
| bush varieties only: attitude of petiole (excluding lower external leaves) | semi-erect (Arlesa) | semi-erect to horizontal |
| 7. Leaves | | |
| blade shape | reniform | reniform |
| blade form | deep lobed | deep lobed |
| margin | dentate | denticulate |

TABLE 3-continued

Physiological and Morphological Characteristics of Line LEB-EH-08-877

| CHARACTERISTIC | LEB-EH-08-877 | Comparison Variety Anita |
|---|---|---|
| margin edges | frilled | frilled |
| average width | 36.3 cm | 38.4 cm |
| average length | 26.7 cm | 29.6 cm |
| leaf surface | blistered | blistered |
| dorsal surface pubescence | soft hairy | bristled |
| vental surface pubescence | soft hairy | bristled |
| color | dark green | dark green |
| color (RHS Color Chart) | N189A | 147A |
| leaf blotching | blotched with gray | blotched with gray |
| leaf blade: size | large (Kriti) | medium |
| leaf blade: incisions | shallow (Everest) | medium |
| leaf blade: intensity of green color of upper surface | dark (Everest) | dark |
| leaf blade: silvery patches | present (Civac) | present |
| leaf blade: relative area covered by silvery patches | small (Aziz) | large |
| average petiole length | 33.4 cm | 39.7 cm |
| petiole length | long (Autumn Gold, Baikal) | medium |
| petiole: number of prickles | many (White Bush Scallop) | many |
| 8. Flower | | |
| pistillate flower: average diameter | 13.3 cm | 13.2 cm |
| pistillate flower: ovary | turbinate | drum-like |
| pistillate flower: average pedicel length | 1.1 cm | 6.5 cm |
| pistillate flower: margin shape | curved | curved |
| pistillate flower: margin edges | frilled | frilled |
| pistillate flower: average sepal width | 0.9 mm | 1.3 mm |
| pistillate flower: average sepal length | 8.6 mm | 6.5 mm |
| pistillate flower: color | deep yellow orange | orange |
| pistillate flower: color (RHS Color Chart) | 21A | 23A |
| staminate flower: average sepal length | 21.2 mm | 17.1 mm |
| staminate flower: average sepal width | 3.0 mm | 2.7 mm |
| staminate flower: average pedicel length | 173.6 mm | 169.6 mm |
| staminate flower: color | deep yellow orange | orange |
| female flower: ring at inner side of corolla | present (Aurore) | present |
| female flower: color of ring at inner side of corolla | green (Aurore, Early White Bush Scallop, President) | green |
| female flower: intensity of green color of ring at inner side of corolla (varieties with green ring at inner side of corolla) | medium (Samba, Senator) | weak |
| male flower: ring at inner side of corolla | present (Goldi) | present |
| male flower: color of ring at inner side of corolla | green (Austral, Belor, Goldi) | yellow and green |
| male flower: intensity of green color of ring at inner side of corolla | strong (Goldi) | |
| staminate flower: color | 21A | orange |
| 9. Fruit | | |
| market maturity: average length | 11.3 cm | 16.1 cm |
| market maturity: average width - stem end | 2.9 cm | 3.2 cm |
| at market maturity: average width - blossom end | 2.1 cm | 2.2 cm |
| market maturity: average weight | 196.3 gm | 354.6 gm |

TABLE 3-continued

Physiological and Morphological Characteristics of Line LEB-EH-08-877

| CHARACTERISTIC | LEB-EH-08-877 | Comparison Variety Anita |
|---|---|---|
| market maturity: shape according to variety type | buttercup | butternut |
| market maturity: apex | rounded | rounded |
| market maturity: base | rounded | rounded |
| market maturity: ribs | inconspicuous | inconspicuous |
| market maturity: rib furrow depth | shallow | shallow |
| market maturity: rib furrow width | medium wide | narrow |
| market maturity: fruit surface | smooth | fine wrinkle |
| market maturity: warts | none | none |
| market maturity: blossom scar button | raised acorn | raised acorn |
| young fruit: ratio length/maximum diameter (zucchini type varieties) | medium (Cora) | medium |
| young fruit: general shape (zucchini and rounded zucchini type varieties) | pear shaped (Clarita) | tapered elliptical |
| young fruit: main color of skin (excluding color of ribs or grooves) | green (Elite, Opal, Romano) | green |
| young fruit: intensity of green color of skin (only varieties with green color of skin) | light (Arlika) | light |
| general shape | pear shaped | club shaped |
| length (zucchini type varieties) | medium (Cora) | medium |
| maximum diameter (zucchini type varieties) | medium (Opal) | medium |
| ratio length/maximum diameter (zucchini type varieties) | medium (Cora) | medium |
| blossom end (zucchini and neck type varieties) | rounded | rounded |
| grooves | absent | absent |
| ribs | absent | absent |
| protrusion of ribs | | |
| main color of skin (excluding color of dots, patches, stripes and bands) | green (Ambassador, Baby Bear) | green |
| intensity of green color of skin (only varieties with green color of skin) | light | light |
| stripes in grooves | absent (Baby Bear, Jack Be Little) | absent |
| dots | present (Gold Rush, Table Queen) | present |
| size of main dots | large (Kingsize) | very large |
| secondary green color between ribs (excluding dots) | absent (Grey Zucchini, Small Sugar) | absent |
| warts on skin | absent | absent |
| size of flower scar | medium (Spidi) | medium |
| length of peduncle | short (Clarita) | medium |
| color of peduncle | green (Ambassador) | green |
| intensity of green color of peduncle | light (Bianchini) | medium |
| mottling of peduncle | present (Elite) | present |
| ripe fruit: secondary color of skin (excluding color of mottles, patches, stripes and bands) | whitish (White Bush Scallop) | yellow |
| ripe fruit: intensity of main color of skin (only yellow and orange) | light | medium |
| secondary color of skin | cream | cream |
| green hue | absent (Jedida) | absent |
| ripe fruit: color of flesh | cream (Elite) | yellow |
| ripe fruit: lignified rind | present (Elite, Little Gem, Scallopini, Yellow Summer Crookneck) | present |

TABLE 3-continued

Physiological and Morphological Characteristics of Line LEB-EH-08-877

| CHARACTERISTIC | LEB-EH-08-877 | Comparison Variety Anita |
|---|---|---|
| ripe fruit: structure of flesh | fibrous (Vegetable Spaghetti) | fibrous |
| 10. Rind | | |
| average thickness at medial | 1.7 mm | 2.2 mm |
| toughness | hard | hard |
| overall color pattern | regular | regular |
| main or ground color | yellow | yellowish-orange |
| main or ground color (RHS Color Chart) | 8D | 18D |
| color of stripes | creamy-white | creamy-orange |
| RHS Color Chart for spots color | 155A | 20C |
| pattern of spots | not specific | not specific |
| 11. Flesh | | |
| average blossom end thickness | 48.8 mm | 60.3 mm |
| average medial thickness | 51.1 mm | 55.6 mm |
| average stem end thickness | 45.5 mm | 44.4 mm |
| texture (fine, granular, lumpy or stringy) | fine | fine |
| texture (soft, firm or brittle) | firm | firm |
| texture (dry, moist or juicy) | juicy | juicy |
| flavor | sweet | sweet |
| quality | excellent | good |
| color | creamy-white | creamy-white |
| color (RHS Color Chart) | 155A | 155B |
| 12. Seed Cavity | | |
| average length | 18.1 cm | 24.6 cm |
| average width | 8.1 cm | 7.9 cm |
| location | conforms to fruit shape | conforms to fruit shape |
| placental tissue | abundant | moderately abundant |
| center core | inconspicuous | prominent |
| 13. Fruit Stalks | | |
| average length | 2.0 cm | 3.2 cm |
| average diameter | 2.8 cm | 2.4 cm |
| cross-section shape | irregular | irregular |
| twisting | not twisted | not twisted |
| tapering | not tapered | tapered |
| straightness | straight | slightly curved |
| texture | spongy | hard |
| furrows | shallow | deep |
| surface | spiny | spiny |
| attachment end | slightly expanded | expanded |
| detaches | with difficulty | with difficulty |
| color | light green | medium green |
| color (RHS Color Chart) | 144B | 143A |
| 14. Seeds | | |
| average length | 15.6 mm | 16.8 mm |
| average width | 9.8 mm | 9.8 mm |
| average thickness | 3.4 mm | 3.3 mm |
| face surface | smooth | smooth |
| color | cream | cream |
| color (RHS Color Chart) | 158B | 155A |
| luster | glossy | glossy |
| margin | curved | curved |
| margin edge | rounded | rounded |
| separation from pulp | difficult | easy |
| average grams per 100 seeds | 16.0 gm | 18.0 gm |
| average number of seeds per fruit | 170.4 | 138.6 |
| seed coat | normal | normal |
| size | medium (Diamant) | large |
| shape | elliptic (Elite) | elliptic |
| hull | present (Baby Bear, Elite) | present |
| appearance of hull | fully developed (Elite) | fully developed |
| color of hull | cream (De Nice à Fruit Rond) | cream |

TABLE 3-continued

Physiological and Morphological Characteristics of Line LEB-EH-08-877

| CHARACTERISTIC | LEB-EH-08-877 | Comparison Variety Anita |
|---|---|---|
| fruit type: | zucchini | |
| fruit: patches, stripes or bands in ripe stage (if zucchini type) | absent (Ambassador, Black Jack) | |

*These are typical values. Values may vary due to environment. Other values that are substantially equivalent are also within the scope of the invention.

C. Breeding Squash Plants

One aspect of the current invention concerns methods for producing seed of squash hybrid SV0201YL involving crossing squash lines LEB-EH-08-877 and ZGN-130-1091. Alternatively, in other embodiments of the invention, hybrid SV0201YL, line LEB-EH-08-877, or line ZGN-130-1091 may be crossed with itself or with any second plant. Such methods can be used for propagation of hybrid SV0201YL and/or the squash lines LEB-EH-08-877 and ZGN-130-1091, or can be used to produce plants that are derived from hybrid SV0201YL and/or the squash lines LEB-EH-08-877 and ZGN-130-1091. Plants derived from hybrid SV0201YL and/or the squash lines LEB-EH-08-877 and ZGN-130-1091 may be used, in certain embodiments, for the development of new squash varieties.

The development of new varieties using one or more starting varieties is well known in the art. In accordance with the invention, novel varieties may be created by crossing hybrid SV0201YL followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with SV0201YL and/or squash lines LEB-EH-08-877 and ZGN-130-1091 for the purpose of developing novel squash lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of squash plants developed by this invention.

D. Performance Characteristics

As described above, hybrid SV0201YL exhibits desirable traits, as conferred by squash lines LEB-EH-08-877 and ZGN-130-1091. The performance characteristics of hybrid SV0201YL and squash lines LEB-EH-08-877 and ZGN-130-1091 were the subject of an objective analysis of the performance traits relative to other varieties. The results of the analysis are presented below.

TABLE 4

Performance Data of Hybrid SV0201YL and Comparative Variety ESKENDERANY
The SV0201YL hybrid was first created in 2009, and evaluations of the hybrid were made in 2010, 2011, and 2012. The results from the Jordan Valley in early 2011 (low pressure of viral diseases) are typical for performance:

| Hybrid | Fruit Shape | Fruit Color | Fruit Uniformity | Blossom Scar | Ease of Harvest | Vigor | Growth Habit | Spines | Marketable fruit/plant |
|---|---|---|---|---|---|---|---|---|---|
| SV0201YL | 5 | 3 | 3 | 4 | 4 | 2 | 4 | 5 | 8.3 |
| SV0201YL | 5 | 4 | 3 | 5 | 5 | 2 | 4 | 4 | 7.5 |
| SV0201YL | 5 | 3 | 2 | 5 | 2 | 2 | 3 | 4 | 9.2 |
| ESKENDERANY | 5 | 6 | 2 | 2 | 2 | 3 | 3 | 6 | 9.0 |
| ESKENDERANY | 5 | 6 | 2 | 3 | 3 | 3 | 3 | 6 | 9.8 |
| ESKENDERANY | 6 | 5 | 3 | 3 | 3 | 4 | 2 | 4 | 7.6 |

TABLE 5

Performance Data of Hybrid SV0201YL and Comparative Variety ESKENDERANY
Also typical for performance under moderate virus pressure are the following results from Los Mochis, Mexico, in 2011:

| ASRT3 | Fruit Shape | Fruit Color | Fruit Uniformity | Blossom Scar | Vigor | Growth Habit | Spines | Marketable fruit/plant |
|---|---|---|---|---|---|---|---|---|
| Eskenderany | 4 | 3 | 6 | 5 | 4 | 4 | 7 | 13.0 |
| Eskenderany | 5 | 4 | 5 | 5 | 6 | 2 | 8 | 9.9 |
| SV0201YL | 3 | 2 | 4 | 6 | 3 | 5 | 6 | 14.1 |
| SV0201YL | 4 | 2 | 8 | 7 | 3 | 4 | 5 | 15.5 |

Traits were observed on a sliding scale, where 1 is ideal and 9 is unacceptable.

E. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those squash plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental squash plant which contributes the locus for the desired characteristic is termed the nonrecurrent or donor parent. This terminology refers to the fact that the nonrecurrent parent is used one time in the backcross protocol and therefore does not recur. The parental squash plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a squash plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny squash plants of a backcross in which a plant described herein is the recurrent parent comprise (i) the desired trait from the non-recurrent parent and (ii) all of the physiological and morphological characteristics of squash the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of squash plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107: 462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); 1 the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a squash plant according to the invention. Non-limiting examples of particular genes and corresponding phenotypes one may choose to introduce into a squash plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic.

In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a squash variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a squash plant by transformation.

H. Deposit Information

A deposit of squash hybrid SV0201YL and inbred parent lines LEB-EH-08-877 and ZGN-130-1091, disclosed above and recited in the claims, has been made with the American Type Culture Collection (ATCC), 10801 University Blvd., Manassas, Va. 20110-2209. The date of deposit were Nov. 20, 2012, Nov. 4, 2013, and Nov. 20, 2012, respectively. The accession numbers for those deposited seeds of squash hybrid SV0201YL and inbred parent lines LEB-EH-08-877 and ZGN-130-1091 are ATCC Accession No. PTA-13335, ATCC Accession No. PTA-120694, and ATCC Accession No. PTA-13334, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A squash plant comprising at least a first set of the chromosomes of squash line LEB-EH-08-877 or squash line ZGN-130-1091, a sample of seed of said lines having been deposited under ATCC Accession Number PTA-120694 and ATCC Accession Number PTA-13334, respectively.

2. A seed comprising at least a first set of the chromosomes of squash line LEB-EH-08-877 or squash line ZGN-130-1091, a sample of seed of said lines having been deposited under ATCC Accession Number PTA-120694 and ATCC Accession Number PTA-13334, respectively.

3. The plant of claim 1, which is inbred.

4. The plant of claim 1, which is hybrid.

5. The seed of claim 2, which is inbred.

6. The seed of claim 2, which is hybrid.

7. The plant of claim 4, wherein the hybrid plant is squash hybrid SV0201YL, a sample of seed of said hybrid SV0201YL having been deposited under ATCC Accession Number PTA-13335.

8. The seed of claim 6, defined as a seed of squash hybrid SV0201YL, a sample of seed of said hybrid SV0201YL having been deposited under ATCC Accession Number PTA-13335.

9. The seed of claim 2, defined as a seed of line LEB-EH-08-877 or line ZGN-130-1091.

10. A plant part of the plant of claim 1, said plant part comprising at least a first set of the chromosomes of squash line LEB-EH-08-877 or squash line ZGN-130-1091, a sample of seed of said lines having been deposited under ATCC Accession Number PTA-120694 and ATCC Accession Number PTA-13334, respectively.

11. The plant part of claim 10, further defined as a leaf, an ovule, pollen, a fruit, or a cell.

12. A squash plant having all the physiological and morphological characteristics of the squash plant of claim 7.

13. A tissue culture of regenerable cells of the plant of claim 1, said cells comprising at least a first set of the chromosomes of squash line LEB-EH-08-877 or squash line ZGN-130-1091, a sample of seed of said lines having been deposited under ATCC Accession Number PTA-120694 and ATCC Accession Number PTA-13334, respectively.

14. The tissue culture according to claim 13, comprising cells or protoplasts from a plant part selected from the group consisting of embryos, meristems, cotyledons, pollen, leaves, anthers, roots, root tips, pistil, flower, seed and stalks.

15. A squash plant regenerated from the tissue culture of claim 13.

16. A method of vegetatively propagating the plant of claim 1, said method comprising the steps of:
    (a) collecting tissue capable of being propagated from a plant according to claim 1;
    (b) cultivating said tissue to obtain proliferated shoots; and
    (c) rooting said proliferated shoots to obtain rooted plantlets.

17. The method of claim 16, further comprising growing at least a first plant from said rooted plantlets.

18. A method of introducing a desired trait into a squash line, said method comprising:
    (a) crossing a plant of line LEB-EH-08-877 or ZGN-130-1091 with a second squash plant that comprises a desired trait to produce F1 progeny, a sample of seed of said lines having been deposited under ATCC Accession Number PTA-120694, and ATCC Accession Number PTA-13334, respectively;
    (b) selecting an F1 progeny that comprises the desired trait;
    (c) backcrossing the selected F1 progeny with a plant of line LEB-EH-08-877 or ZGN-130-1091 to produce backcross progeny;
    (d) selecting backcross progeny comprising the desired trait; and
    (e) repeating steps (c) and (d) three or more times to produce selected fourth or higher backcross progeny that comprise the desired trait and otherwise comprises all of the morphological and physiological characteristics of line LEB-EH-08-877 or ZGN-130-1091.

19. A method of producing a plant comprising an added trait, the method comprising introducing a transgene conferring the trait into a plant of hybrid SV0201YL, line LEB-EH-08-877 or line ZGN-130-1091, a sample of seed of said hybrid and lines having been deposited under ATCC Accession Number PTA-13335, ATCC Accession Number PTA-120694, and ATCC Accession Number PTA-13334, respectively.

20. A plant of squash hybrid SV0201YL, line LEB-EH-08-877 or line ZGN-130-1091, further comprising a transgene, wherein a sample of seed of said hybrid and line having been deposited under ATCC Accession Number PTA-13335, ATCC Accession Number PTA-120694, and ATCC Accession Number PTA-13334, respectively, and wherein the plant otherwise comprises all of the morphological and physiological characteristics of squash hybrid SV0201YL, line LEB-EH-08-877 or line ZGN-130-1091.

21. The plant of claim 20, wherein the transgene confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

22. A plant produced by introducing a single locus conversion into a plant of squash line LEB-EH-08-877 or line ZGN-130-1091, wherein the converted plant comprises the single locus conversion and otherwise comprises all of the morphological and physiological characteristics of squash line LEB-EH-08-877 or line ZGN-130-1091, a sample of seed of squash line LEB-EH-08-877 and line ZGN-130-1091 having been deposited under ATCC Accession Number PTA-120694, and ATCC Accession Number PTA-13334, respectively.

23. The plant of claim 22, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

24. A method for producing a seed of a plant derived from at least one of hybrid SV0201YL, line LEB-EH-08-877 or line ZGN-130-1091, said method comprising the steps of:
    (a) crossing a squash plant of hybrid SV0201YL, line LEB-EH-08-877 or line ZGN-130-1091 with itself or a second squash plant; a sample of seed of said hybrid and lines having been deposited under ATCC Accession Number PTA-13335, ATCC Accession Number PTA-120694, and ATCC Accession Number PTA-13334, respectively; and
    (b) allowing seed of a hybrid SV0201YL, line LEB-EH-08-877 or line ZGN-130-1091-derived squash plant to form.

25. The method of claim 24, further comprising the steps of:
    (c) selfing a plant grown from said hybrid SV0201YL, LEB-EH-08-877 or ZGN-130-1091-derived squash seed to yield additional hybrid SV0201YL, line LEB-EH-08-877 or line ZGN-130-1091-derived squash seed;
    (d) growing said additional hybrid SV0201YL, line LEB-EH-08-877 or line ZGN-130-1091-derived squash seed of step (c) to yield additional hybrid SV0201YL, line LEB-EH-08-877 or line ZGN-130-1091-derived squash plants; and
    (e) repeating the crossing and growing steps of (c) and (d) to generate at least a first further hybrid SV0201YL, line LEB-EH-08-877 or line ZGN-130-1091-derived squash plant.

26. The method of claim 24, wherein the second squash plant is of an inbred squash line.

27. The method of claim 24, comprising crossing line LEB-EH-08-877 with line ZGN-130-1091, a sample of seed of said lines having been deposited under ATCC Accession Number PTA-120694, and ATCC Accession Number PTA-13334, respectively.

28. The method of claim 25, further comprising:
    (f) crossing the further hybrid SV0201YL, LEB-EH-08-877 or ZGN-130-1091-derived squash plant with a second squash plant to produce seed of a hybrid progeny plant.

29. A plant part of the plant of claim 7, wherein the plant part comprises a cell of squash hybrid SV0201YL.

30. The plant part of claim 29, further defined as a leaf, a flower, a fruit, an ovule, pollen, or a cell.

31. A method of producing a squash seed, said method comprising crossing the plant of claim 1 with itself or a second squash plant and allowing seed to form.

32. A method of producing a squash fruit, said method comprising:
  (a) obtaining a plant according to claim 1, wherein the plant has been cultivated to maturity; and
  (b) collecting a squash from the plant.

\* \* \* \* \*